United States Patent [19]

Feijen et al.

[11] Patent Number: 5,061,750

[45] Date of Patent: Oct. 29, 1991

[54] COVALENT ATTACHMENT OF ANTICOAGULANTS AND THE LIKE ONTO BIOMATERIALS

[75] Inventors: Jan Feijen, Hengelo; Gerardus H. M. Engbers, Oldenzaal, both of Netherlands

[73] Assignee: Cordis Europa N.V., Roden, Netherlands

[21] Appl. No.: 555,664

[22] Filed: Jul. 18, 1990

Related U.S. Application Data

[63] Continuation of Ser. No. 200,655, May 31, 1988, abandoned.

[30] Foreign Application Priority Data

Jun. 9, 1987 [NL] Netherlands ............... 8701337

[51] Int. Cl.$^5$ ............... C08G 63/48; C08G 63/91; C12N 11/06; A61F 2/02
[52] U.S. Cl. ............... 525/54.1; 523/112; 435/180; 514/822; 424/422; 424/423
[58] Field of Search ............... 523/112; 525/54.1; 435/180; 514/822; 424/422, 423

[56] References Cited

U.S. PATENT DOCUMENTS

| | | | |
|---|---|---|---|
| 3,826,678 | 7/1974 | Hoffman et al. | 428/420 |
| 4,378,435 | 3/1983 | Takagi et al. | 435/180 |
| 4,521,564 | 6/1985 | Solomon et al. | 523/112 |
| 4,634,762 | 1/1987 | Feijen et al. | 530/350 |

FOREIGN PATENT DOCUMENTS

| | | |
|---|---|---|
| 28122 | 5/1981 | European Pat. Off. |
| 46828 | 10/1982 | European Pat. Off. |
| 2187849 | 1/1974 | France |
| 8700060 | 7/1986 | PCT Int'l Appl. |
| 1583008 | 1/1981 | United Kingdom |

*Primary Examiner*—Thurman K. Page
*Assistant Examiner*—C. Azpuru
*Attorney, Agent, or Firm*—Lockwood, Alex, Fitzgibbon & Cummings

[57] ABSTRACT

A substrate for medical devices and a process for making the substrate is provided, the substrate having on at least part of its surface a blood-compatible surface produced by coupling a physiologically active substance to the surface. The physiologically active substance is one having an inhibitory effect on the formation of blood clots and/or is capable of breaking down blood clots formed. The physiologically active substance is bonded to a polyacid, and the polyacid is attached to the surface by a covalent bond.

30 Claims, 1 Drawing Sheet

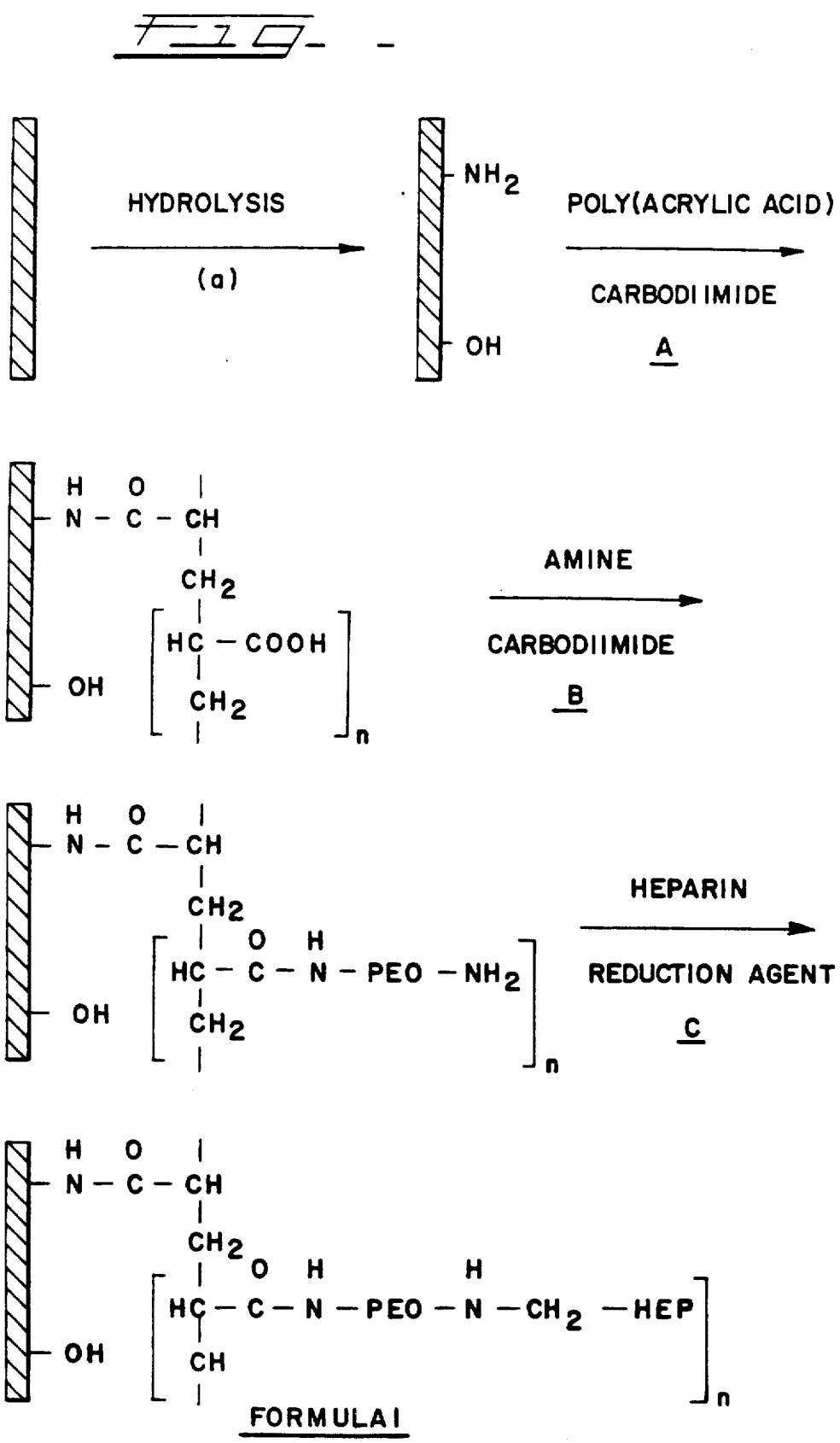

COVALENT ATTACHMENT OF ANTICOAGULANTS AND THE LIKE ONTO BIOMATERIALS

This application is a continuation of application Ser. No. 07/200,655, filed May 31, 1988, now abandoned.

BACKGROUND AND DESCRIPTION OF THE INVENTION

The invention relates to a substrate provided with a blood-compatible surface and to a method of forming same. More particularly, the blood-compatible surface is produced by coupling to at least part of the surface a physiologically active substance having an inhibitory effect on the formation of blood clots or having the capability of breaking down blood clots formed. The coupling includes a polyacid that is covalently bonded to the surface, the physiologically active substance being bonded to the polyacid.

As is known, various attempts have been made to improve the blood compatibility of various kinds of biomaterials by immobilizing on their surface heparin or heparin analogues. Thus it is known from U.S. Pat. No. 4,526,714 to render the surface of a substrate biocompatible by coating it with a conjugate of heparin, heparinous material or heparin analogues and a protein, the conjugate being formed by coupling that is carried out in the presence of 1-ethyl-3-dimethylaminopropyl carbodiimide (EDC) and the like as a coupling agent. The conjugate is attached to the substrate surface at the sites of the surface where free functional groups suitable for binding to the conjugate are present. In order to effect the coupling needed to form this known conjugate, these free functional groups on the substrate surface are provided as free amino groups.

For the blood compatibility of this prior art substrate surface to increase, the degree of coverage of the surface with the conjugate must be increased, which, for all practical purposes, means that the substrate surface should have a similarly large number of free functional groups available which are suitable for binding. Since the surface of a substrate often does not have free functional groups such as amino groups, these groups should first be liberated from the substrate material. This can be effected, for example, by chemical means, which is then accompanied by an attack on, i.e. damage to, the substrate surface. This damage is, of course, more severe as the number of free functional groups that must be provided is increased.

It is a general object of the invention to provide a substrate having a blood-compatible surface, as well as to a process for making the same.

Another object of the invention is to provide a blood-compatible surface in which a large and typically controllable amount of a physiologically active substance is connected via anchoring sites available on the surface of a substrate.

Another object of the present invention is to provide a blood-compatible surface on at least a selected portion of a medical device while avoiding or causing disproportionately little damage to the substrate surface.

These and other objects, features and advantages of this invention will be clearly understood through a consideration of the following detailed description.

In summary, the invention is a substrate having a physiologically active substance covalently bonded to at least a portion of its surface via a polyacid, as well as to a method of making same. The polyacid, which according to the present invention means a polymer containing many free carboxylic acid groups, is covalently bonded to the surface of the substrate, and the physiologically active substance is attached to various of the free carboxylic acid groups of the polyacid.

The invention is based on the insight that, owing to the introduction of a polyacid in the link chain of the physiologically active substance to the substrate surface, the carboxyl groups of each polyacid molecule provide a large number of free functional groups not belonging to the original substrate surface, which can serve as many bonding sites for anchoring the physiologically active substance. Accordingly, although only a small number of functional groups, such as amino groups, are introduced to, or liberated on, the original substrate surface, the number of potential bonding sites for the ultimate substance affecting the coagulation of blood is increased dramatic-ally by the numerous multiple free carboxylic acid functional groups provided by the polyacid.

BRIEF DESCRIPTION OF THE DRAWINGS

In the course of this description, reference will be made to the accompanying FIGURE, which is a formulae sheet exemplifying a typical reaction scheme according to the present invention.

DESCRIPTION OF THE PARTICULAR EMBODIMENTS

Any substrate having a surface that bonds with a polyacid formed or to be formed is suitable according to the invention. One example is a substrate of a material in which the polyacid is directly bonded to the substrate surface and is formed by polymerizing a COOH-group containing monomer from the substrate surface to the polyacid, or in which the polyacid, preferably with a double bond at the chain terminal, is directly attached to the substrate surface by this terminal by means of a graft reaction. Another example is a substrate made from a material suitable for liberating functional groups from the substrate surface thereof. Examples of substrate materials belonging to this category are those having free amino, isocyanate, carboxyl, and/or alcohol groups available as functional groups, or that are capable of providing such groups. The polyacid can be directly coupled to the functional group, for example, if this group is an amino group, or coupling can be achieved after first chemically modifying the functional group, for example, in the case of a carboxyl group, which is first modified by a low-molecular weight diamine before being reacted with the polyacid.

A polyacid suitable for the purposes of the invention is preferably a polyacid that is water-soluble. This type of polyacid may contain an aliphatic main chain to which carboxyl groups are attached, optionally via a side chain. An example of this type of polyacid are polyacrylic acids which may be built up from numerous monomeric units, for example between 1000 and 10,000 units, and in which each monomeric unit accordingly contains one carboxyl group. Polymethacrylic acids are likewise suitable. Also suitable is a polyacid having a non-aliphatic main chain, for example, polyaspartic acid and polyglutamic acid. Furthermore, a polymer can be used that exhibits two or more carboxyl groups per monomer unit. In addition, the substrate according to the present invention may contain a polyacid which is cross-linked.

The physiologically active substance to be used according to the invention is one having an inhibitory effect on the formation of blood clots or has the capability of breaking down blood blots formed. It may be a substance having an anti-coagulant effect, a substance having a fibrinolytic activity, a substance having a blood platelet aggregation inhibiting effect and/or a blood platelet adhesion inhibiting effect. For example, heparin, a heparinoid, a prostaglandin, urokinase, streptokinase or combinations thereof may be used. Heparinous materials typically are used.

Although not necessary, it is advantageous for the substance with an inhibitory effect on the formation of blood clots or capable of breaking down the blood clots formed to be connected via a spacer compound to the polyacid, which itself, for that matter, also functions as a spacer. The spacer compound may be a compound containing more than one $NH_2$ group, for example, a polyethylene oxide containing terminal amino groups. Another suitable spacer compound is, for example, a protein.

The invention also relates to a method of making the substrate with a blood compatible surface. Included is a pre-stage or first step, in which a number of functional groups are liberated from the substrate surface, or are introduced into the substrate surface. In a first stage or second step, the functional group connected to the substrate surface is coupled to a polyacid, and thereafter in a second stage or third step, the physiologically active substance is coupled to the polyacid via a spacer compound containing more than one amino group.

The polyacid may be directly attached to the substrate surface owing to its being formed by polymerizing a monomer from the substrate surface that contains at least one COOH group or owing to having the polyacid attached to the substrate surface via a graft reaction, in which case a polyacid can be used which contains a C=C double bond. It is also possible to use a polyacid containing two or more carboxyl groups per monomer unit, for example, polymaleic acid or an activated precursor of the polyacid, a particular example being a polyacid anhydride.

With reference to the reaction scheme indicated on the accompanying sheet of formulae shown in the FIGURE, the invention and especially the method according to the invention are exemplified by reference thereto. Details of this example of the present invention are as follows.

In the example shown in the FIGURE, a substrate material capable of providing amino groups as free functional groups is used. During a preliminary reaction stage, free amino groups will be liberated. If the substrate material already exhibits free amino groups or the like, this preliminary reaction stage could be omitted. If the substrate material is, for example, a polyetherurethane, the surface thereof can be treated chemically in the manner illustrated by reaction (a) in the FIGURE. For example, such a substrate may be subjected to hydrolysis for about thirty minutes in a 3M solution of NaOH in water at a temperature of about 60° C. In this illustrated reaction, urethane bonds are broken, and amino and hydroxyl groups are formed.

Other methods of introducing free amino groups into the substrate surface are also suitable. For example, free amino groups can be introduced physically by means of so-called "plasma glow discharge", according to which method radicals are formed at the substrate surface of such an elected type that these provide, for example, free $NH_2$ groups in interaction with suitably selected compounds in the gaseous phase.

The free amino groups formed are subsequently covalently bonded to a polyacid, for example, polyacrylic acid in which n=1000 as illustrated in reaction stage (A) in the FIGURE. Based on a substrate surface containing free amino groups, the coupling with the polyacrylic acid can be effectively carried out in the presence of a coupling agent, for example, a carbodiimide. Preferably, a water-soluble carbodiimide is used, because water is not corrosive relative to the substrate material. The function of the coupling agent such as a carbodiimide in the coupling reaction is that in which a portion of the free carboxyl groups of the polyacid are activated by the carbodiimide, and these activated carboxyl groups in turn react with a free $NH_2$ group of the substrate.

The coupling product of the free amino group of the substrate with polyacrylic acid, illustrated in reaction stage (B) of the FIGURE, is subsequently brought into a form in which it can serve as a basis for the ultimate immobilization of a physiologically active substance, for example, heparin, to the substrate surface. For this purpose, the free carboxyl groups of the polyacid are coupled to the polyethylene oxide (PEO) with terminal amino groups. This is illustrated in reaction stage (B) in the FIGURE.

In addition to serving as a supplier of an attachment site for the ultimate physiologically active substance to be immobilized, the amino-terminated polyethylene oxide having more than one amino group is active as a so-called "spacer" group. It is known that physiologically active substances, such as heparin, function better in an environment in which they are relatively more mobile than one in which they are immobilized, such as being attached to a substrate. A direct coupling of heparin or the like to the substrate surface immobilizes same to a great extent, as a result of which its physiological activity is reduced. Accordingly, the polyethylene oxide functions as a "spacer" group to provide additional space between the physiologically active substance and the substrate surface to which it is ultimately bonded.

Inasmuch as the reaction indicated in reaction stage (B) of the FIGURE is of a type along the lines of reaction stage (A), the coupling according to reaction stage (B) can also be effectively carried out in the presence of a coupling agent such as a carbodiimide when desired.

In a last stage which is illustrated in the FIGURE as reaction stage (C), which is in accordance with the preferred embodiment, a heparin (HEP) containing a terminal aldehyde group is attached. The aldehyde group forms a Schiff's base with the free amino group of the amino-terminated polyethylene oxide. This Schiff's base can be reduced to form a stable secondary amine by means of sodium cyanoborohydride. The reaction product obtained by following the reaction scheme illustrated in the FIGURE is the reaction product having Formulae 1, which is bonded to the substrate surface.

It is also possible to vary the reaction sequence. For example, one could first react a heparinous material containing a terminal aldehyde group with an excess of non-bonded amino-terminated polyethylene oxide in the presence of a reducing agent, such as sodium cyanoborohydride. Subsequently, the reaction product thus obtained is coupled via the free amino group of the polyethylene oxide moiety of the molecules of the reaction product to the polyacid whose carboxylic acid groups have been pre-activated by means of, for example, a water-soluble carbodiimide.

As stated before, in addition to heparin, other blood coagulation affecting substances may be bonded to the reaction product having Formula 1. Thus, for example, when a polyacrylic acid with 1000 monomer units is used, it is possible to realize such a distribution that, in the reaction product having Formula 1, a molar ratio of 75% heparin and 25% other physiologically active substances is possible, for example.

By rendering a substrate surface biocompatible in accordance with the present invention, various advantages can be realized. Due to the use of the polyacid, as much of a physiologically active substance, such as a blood coagulation affecting substance, for example heparin, can be bonded to the substrate as is considered desirable. The extent or relative amount of physiologically active substance that can be bonded to a substrate, for example a catheter, will generally depend on the molecular weight of the polyacid and can be generally controlled to assure blood compatibility of the substrate.

In addition, as is exemplified in reaction stage (A) of the FIGURE, the use of a polyacid and the reaction for liberating functional groups, for example to provide amino groups, does not necessarily have a particularly high efficiency. In the case of hydrolysis of a polyetherurethane surface, this means, for all practical purposes, that it is not necessary to split a large amount of chains, so that surface damage can be reduced, while the introduction of functional groups at the substrate surface only needs to take place on a limited scale. Furthermore, instead of effecting a direct coupling of the spacer compound to the substrate surface, the use of the polyacid permits an increase in the mobility o the coupled blood coagulation affecting substrate such as heparinous material. This mobility is of importance for the anti-coagulant effect of the bonded physiologically active substance or substances.

It will be understood that the embodiments of the present invention which have been described are illustrative of some of the applications of the principles of the present invention. Numerous modifications may be made by those skilled in the art without departing from the true spirit and scope of the invention.

We claim:

1. In a substrate component of a synthetic medical device, said substrate component having a polymeric surface, at least a part of said polymeric substrate surface being for contacting blood when the medical device is in use, said blood-contacting polymeric substrate surface having a physiologically active substance which has an inhibitory effect on the formation of blood clots or is capable of breaking down blood clots formed, wherein the improvement comprises:
   said physiologically active substrate is graft bonded to said polymeric substrate surface through a polyacid link chain moiety, said polyacid being a polymer containing from between about 1000 and 10,000 monomeric units which contain a carboxyl group, said bond being through a plurality of said monomeric unit carboxyl groups of the polyacid, said link chain polyacid is bonded to said polymeric substrate surface by a chemical bond, and said chemical bond is a covalent bond between a functional group of the link chain polyacid and a functional group of said polymeric substrate surface; and
   said physiologically active substance is selected from the group consisting of a substrate having an anticoagulant effect, a non-synthetic substance having a fibrinolytic activity, a substance having a blood platelet aggregation inhibiting effect, a substance having a blood platelet adhesion inhibiting effect, and combinations thereof.

2. The substrate as claimed in claim 1, wherein said polyacid is soluble in an aqueous medium.

3. The substrate as claimed in claim 1, wherein said polyacid includes an aliphatic main chain to which carboxylic groups are attached.

4. The substrate as claimed in claim 3, wherein said polyacid is polyacrylic acid or polymethacrylic acid.

5. The substrate as claimed in claim 2, wherein said polyacid is polyaspartic acid.

6. The substrate as claimed in claim 2, wherein said polyacid is polyglutamic acid.

7. The substrate as claimed in claim 1, wherein said polyacid is cross-linked.

8. The substrate as claimed in claim 1, wherein said physiologically active substance is bonded to the polyacid via a spacer compound.

9. The substrate as claimed in claim 8, wherein said spacer compound is a compound containing more than one $NH_2$ group.

10. The substrate as claimed in claim 9, wherein said spacer compound is polyethylene containing terminal amino groups.

11. The substrate as claimed in claim 9, wherein said spacer compound is a protein containing terminal amino groups.

12. The substrate as claimed in claim 1, wherein said physiologically active substance is selected from the group consisting of a heparin, a heparin compound, heparinous material, a prostaglandin, urokinase, streptokinase and combinations thereof.

13. The substrate as claimed in claim 12, wherein said physiologically active substance is a heparin with a high affinity for anti-thrombin III and/or a low interaction with blood platelets.

14. A method of making a medical device, at least a part of a surface of the substrate having a physiologically active substance which has an inhibitory effect on the formation of blood clots or is capable of breaking down blood clots formed wherein the method comprises:
   a preliminary stage in which a number of functional groups are bonded to the substrate surface by being liberated from or introduced at the substrate surface;
   a first stag in which the functional group bonded to the substrate surface is covalently coupled to a polyacid; and
   a second stage after said first stage wherein a physiologically active substance is bonded to the polyacid.

15. The method as claimed in claim 14 further including a step of attaching a spacer compound to the polyacid and to the physiologically active substance so that the physiologically active substance is bonded to the polyacid via the spacer compound.

16. The method as claimed in claim 15, wherein said step of attaching a spacer compound utilizes a spacer compound containing more than one amino group, and wherein one of the amino groups attaches to the polyacid and another of the amino groups attaches to the physiologically active compound.

17. The method as claimed in claim 14, wherein the preliminary stage includes directly attaching the polyacid to the substrate surface.

18. The method as claimed in claim 17, wherein said polyacid is formed by polymerizing a monomer from the substrate surface, which monomer includes a COOH group.

19. The method as claimed in claim 17, wherein said direct attaching of the polyacid to the substrate surface includes a graft reaction.

20. The method as claimed in claim 14, wherein said graft reaction includes reacting a polyacid that has a C=C double bond.

21. The method as claimed in claim 14, wherein said first stage includes using a polyacid containing two or more carboxyl groups per monomer unit.

22. The method as claimed in claim 14, wherein said first stage includes using an activated precursor of the polyacid.

23. The method as claimed in claim 22 wherein said activated precursor of the polyacid is a polyacid anhydride.

24. The method as claimed in claim 15, wherein said step of attaching a spacer compound includes providing a heparin containing a terminal aldehyde group as the physiologically active substance and providing a spacer compound containing more than one amino group, further including coupling said physiologically active substance to said spacer compound in the presence of a reducing agent.

25. The method as claimed in claim 24, wherein said heparin containing a terminal aldehyde group is first reacted with an excess of the spacer compound containing more than one amino group in the presence of the reducing agent to form a resulting reaction product, pre-activating carboxylic acid groups of the polyacid, and coupling said resulting reaction product to the polyacid whose carboxylic acid groups have been pre-activated, said coupling being via another amino group of the spacer compound.

26. The method as claimed in claim 24, further including using sodium cyanoborohydride as the reducing agent.

27. The method as claimed in claim 14, further including using a coupling agent in the first stage during coupling of the polyacid with an amino group as the functional group.

28. The method as claimed in claim 27 wherein the coupling agent is a carbodiimide.

29. The method as claimed in claim 15, wherein said attaching of the spacer compound containing more than one amino group to the polyacid is carried out in the presence of a coupling agent.

30. The method as claimed in claim 29, wherein the coupling agent is selected from the group consisting of a carbodiimide and another coupling agent for forming an amide group according to peptide chemistry.

* * * * *

UNITED STATES PATENT AND TRADEMARK OFFICE
CERTIFICATE OF CORRECTION

PATENT NO. : 5,061,750
DATED : October 29, 1991
INVENTOR(S) : Jan Feijen and Gerardus H. M. Engbers It is certified that error appears in the above-indentified patent and that said Letters Patent is hereby corrected as shown below:

Col. 2, line 19, "dramatic-ally" should read --dramatically--.
Col. 5, line 36, "o" should read --of--.
Col. 6, line 4, "substrate" should read --substance--; line 30, "polyethylene containing" should read --polyethylene oxide containing--; line 54, "stag" should read --stage--.
Col. 7, line 13, "claim 14" should read --claim 19--; line 25, "claim 15" should read --claim 16--.
Col. 8, line 22, "claim 15" should read --claim 16--.

Signed and Sealed this

Twenty-third Day of May, 1995

Attest:

BRUCE LEHMAN

Attesting Officer     Commissioner of Patents and Trademarks